United States Patent [19]

Padden et al.

[11] Patent Number: 4,631,187

[45] Date of Patent: Dec. 23, 1986

[54] HAIR TREATING COMPOSITION CONTAINING A QUATERNARY AMMONIUM COMPOUND CONTAINING AN ERUCYL GROUP

[75] Inventors: Timothy J. Padden; Heidi J. Uick, both of Racine, Wis.

[73] Assignee: S.C. Johnson & Son, Inc., Racine, Wis.

[21] Appl. No.: 426,460

[22] Filed: Sep. 29, 1982

[51] Int. Cl.$^4$ ............................ A61K 7/06; A61K 7/09
[52] U.S. Cl. ............................ 424/70; 424/DIG. 4; 424/71; 514/642; 514/852
[58] Field of Search ............ 424/70, 329, 71, DIG. 1, 424/DIG. 4

[56] References Cited

U.S. PATENT DOCUMENTS

| | | | |
|---|---|---|---|
| 3,311,659 | 3/1967 | Birkelo et al. | 424/70 X |
| 3,395,100 | 7/1968 | Fisher et al. | 252/88 R |
| 3,580,853 | 5/1971 | Parran, Jr. | 424/78 |
| 3,686,416 | 8/1972 | Myer et al. | 424/329 |
| 4,035,478 | 7/1977 | Mullen | 424/70 |
| 4,069,347 | 1/1978 | McCarthy et al. | 424/358 |
| 4,102,795 | 7/1978 | Minegishi et al. | 424/70 |
| 4,134,970 | 1/1979 | Panke et al. | 424/70 |
| 4,144,326 | 3/1979 | Luedicke et al. | 424/70 |
| 4,149,551 | 4/1979 | Benjamin et al. | 424/70 |
| 4,183,917 | 1/1980 | Iwao et al. | 424/70 |
| 4,325,940 | 4/1982 | Green et al. | 424/329 |
| 4,369,037 | 1/1983 | Matsunaga et al. | 424/70 |

FOREIGN PATENT DOCUMENTS

| | | | |
|---|---|---|---|
| 5103364 | 8/1980 | Japan | 424/325 |
| 5103365 | 8/1980 | Japan | 424/325 |

OTHER PUBLICATIONS

Humko Sheffield Bulletin, 1979, pp. 1 and 2.
Egan et al, American Perfumer & Cosmetics, 10/1968, vol. 83, No. 10, pp. 55 to 58.
The Merck Index, 1976, 9th edition, 3594.

Primary Examiner—Dale R. Ore

[57] ABSTRACT

A hair care product containing in an aqueous base a quaternary compound having one erucic group. These compositions provide creme rinse formulations which have good conditioning properties and at the same time good, clean feel.

8 Claims, No Drawings

HAIR TREATING COMPOSITION CONTAINING A QUATERNARY AMMONIUM COMPOUND CONTAINING AN ERUCYL GROUP

BACKGROUND

This invention relates to novel hair care compositions. More particularly, this invention relates to hair care compositions designed for use as cream rinses and other hair-treating compositions containing an erucyl quaternary compound.

Various quaternary compounds have been long-known for use in cream rinse and hair conditioner compositions. Typically, these materials have one or more long chain fatty groups. These long chain fatty groups typically are saturated and have 18 or fewer carbon atoms. There have also been attempts to prepare cream rinse and conditioning compositions which are essentially clear, i.e., they are transparent or translucent and not opaque. It is felt by consumers that these transparent formulations imply a hair care product which will leave the hair feeling cleaner.

There are a number of known quaternary compounds which have not been utilized as hair care products. These materials often are utilized as fabric softeners, yarn lubricants, germicides and the like. These quaternary compounds often utilize a variety of different groups. However, for one reason or another, these materials have not been tried or used in hair care products. Reasons for this may be toxicology, solubility characteristics, cost and similar considerations.

BRIEF DESCRIPTION OF THE INVENTION

It has been found that a certain class of quaternary compound which includes a long chain single unsaturated fatty group produces cream rinse and conditioning compositions having surprising clean feel properties on the hair along with good conditioning and fly-away reduction properties. It has also been found that this same quaternary compound can be formulated into cream rinse and conditioning compositions which are substantially clear or transluscent and are compatible with anti-dandruff agents.

OBJECTS AND ADVANTAGES

It is, therefore, a primary object of the present invention to provide cream rinse and conditioning compositions which produce a good clean feel on the hair after use, along with good conditioning and antistatic properties.

It is a further object and advantage of the present invention to provide cream rinse and conditioning compositions which have good wet combing properties.

It is a still further object of the present invention to provide cream rinse and conditioning compositions which are essentially clear or transluscent.

It is a still further object of the present invention to provide a cream rinse and conditioning composition which can also incorporate an antidandruff agent.

Still further objects and advantages of the products of the present invention will become more apparent from the following more detailed description thereof.

DETAILED DESCRIPTION

The present invention relates to a hair-treating composition comprising:
(a) An aqueous base and
(b) An effective amount of a quaternary ammonium compound having the formula

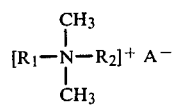

wherein $R_1$ is a mixture of $C_{18}$ to $C_{24}$ alkyls and $C_{18}$ to $C_{24}$ alkenyls, said mixture comprising at least about 65% by weight docosenyl, less than about 15% by weight docosyl and less than about 35% by weight of a mixture of $C_{18}$–$C_{24}$ alkyls other than docosyl and $C_{18}$–$C_{24}$ alkenyls other than docosenyl, $R_2$ is selected from methyl, ethyl and benzyl and A is an anion.

When used in the instant specification and claims, the term "erucic" and "erucyl" relates to a mixed alkenyl having at least about 65% $C_{22}$ olefins derived from erucic acid, cis-13-docosenoic acid.

Suitable quaternary ammonium compounds include those having the formula:

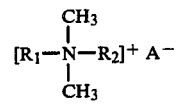

wherein $R_1$ is a mixture of $C_{18}$ to $C_{24}$ alkyls and $C_{18}$ to $C_{24}$ alkenyls, said mixture comprising at least about 65% by weight of docosenyl, less than about 15% by weight cocosyl and less than about 35% by weight of a mixture of $C_{18}$ to $C_{24}$ alkyls other than docosyl and $C_{18}$ to $C_{24}$ alkenyls other than docosenyl, $R_2$ is selected from methyl, ethyl and benzyl and A is an anion.

In the above formula $R_1$ is derived from fatty acids high in $C_{22}$ unsaturated fatty acid, docosenoic acid. As it is very difficult to accurately analyze quaternary compounds for chain length distribution, for the purpose of the present specification and claims, it is assumed that the chain length distribution is unchanged during the reactions to form the quaternary ammonium compound from the fatty acid. Most chain lengths described in literature are described using this assumption, which is standard industrial practice. In order to have sufficient wet combing and clean feel on the hair always with good static control, the fatty acid should have at least about 65% by weight docosenyl. This high percentage of docosenyl makes the resulting quaternary compound more water soluble. A quaternary made from fatty acids with a high saturated alkyl content is generally not water-soluble.

It is preferred that the docosenyl content be at least about 75% by weight for optimum performance in a cream rinse. If a clear cream rinse product is desired, the docosenyl content should be at least about 80% by weight. Conversely, the docosyl content preferably should be less than about 10% by weight and the other $C_{18}$ to $C_{24}$ saturated and unsaturated groups should be less than about 15% by weight. For a clear product the docosyl content should be less than about 9% by weight and the other $C_{18}$ to $C_{24}$ alkyl and alkenyl groups should be less than about 11% by weight.

As noted above, $R_2$ can be methyl, ethyl or benzyl. This is a function of the group used to quaternize the tertiary amine. The preferred group is benzyl.

The anion may be any conventional anion which is suitable for use in a personal care product. The only real limit is toxicity. Suitable anions include chloride, bromide, iodide, ethyl sulfate, methyl sulfate and the like. The preferred anion is chloride.

Quaternary ammonium compounds which are suitable for use in the compositions of the present invention include trimethyl erucyl ammonium chloride, dimethyl ethyl erucyl ammonium ethyl sulfate, trimethyl erucyl ammonium methyl sulfate, dimethyl benzyl erucyl ammonium chloride and the like.

The quaternary compounds of the present invention are commercially available materials available from the Humko Division of Witco Chemical. These materials are prepared using known quaternization techniques.

Although any effective amount of the quaternary can be used in the composition, it is preferred for cost and performance reasons to use from about 0.5 to 10% by weight quaternary in the formulations. The optimum formulations use from about 0.5 to 5% by weight of quaternary.

The compositions of the present invention also include an aqueous base. Within this aqueous base, a wide number of compounds may be included. The prime component of the base material, of course, is water. Either deionized or demineralized water can be utilized with the formulations of the present invention. Other components in the aqueous base include the following: nonionic and cationic surfactants including other quaternary compounds, thickeners, anti-dandruff agents, lower alkanols, fatty alcohols, other hair conditioning agents, cationic polymers, preservatives, perfumes and dyes.

In its simplest form the composition of the present invention includes an aqueous dispersion of the quaternary in water. However, for commercially acceptable formulations, a number of the above additives preferably are included in such a formulation. It is preferred that the combined amounts of these materials be less than about 10% by weight of the composition.

Suitable surfactants include the nonionic and cationic surfactants. These surfactants are present, if at all, in amounts up to about 5% by weight. Suitable nonionic surfactants are those such as the sorbitan monolaurate, sorbitan monopalmitate, sorbitan monostearate, sorbitan monooleate surfactants, as well as the ethoxylated versions of these materials; the polyethylene glycols such as those with 6 to 14 ethylene oxide units, polyethylene polypropylene glycols such as the Pluronics from BASF.

Suitable cationic surfactants include dilaureth (4 ethylene oxide units) dimonium chloride, also sold under the tradename HOE S 2650 (American Hoechst), stearyl dimethyl amine hydrochloride, stearyl amido propyl dimethyl amine lactate, stearyl amido propyl dimethyl amine citrate, and the like.

The aqueous base also may include a small percentage up to about 10% by weight of a lower alkanol. Suitable lower alkanols include methanol, ethanol and propanol, although ethanol is preferred from a toxicity standpoint.

The compositions also include a small and effective amount of an antidandruff agent. Suitable antidandruff agents include piroctone olamine (Trademark-Octopirox), 1-4(4-chlorophenxy)-1-imideol-1-yl-3,3-dimethyl-2-butane, (Climbazole), zinc pyrithone, and the like. Generally, it is found that less than about 5% by weight of these antidandruff agents provide suitable activity.

The compositions also include a small percentage of thickener, generally less than about 3% by weight. Suitable thickeners include hydroxyethyl cellulose, hydroxypropyl cellulose, hydroxypropyl methyl cellulose, and high molecular weight polyethylene oxide polymers. Suitable hydroxyethyl cellulose materials include Natrosol 150 and Natrosol 250 from Hercules, Cellosize QP, Cellosize WP from Union Carbide and the like. Suitable hydroxypropyl cellulose materials include the various grades of Klucel sold by Hercules. Suitable hydroxypropyl methyl cellulose is available under the various grades of Methocel sold by Dow Chemical. Various grades of the high molecular weight glycol materials are available under the tradename Polyox from Union Carbide. It is also possible to salt thicken these formulations using known methods.

The compositions also may include a variety of cationic polymers. These polymers impart a variety of desirable properties to the hair. These polymers are classified by the Cosmetic, Toiletry & Fragrance Assn. in the 3rd edition of *The CTFA Cosmetic Ingredient Dictionary* as polyquateriums. Suitable materials include polyquaterium-5, polyquaterium-6, polyquaterium-7, polyquaterium-10, polyquaterium-11. Also suitable are the aminoethyl acrylate phosphate/acrylate copolymers and quar hydroxypropyltrimonium chloride. Generally, less than about 3% by weight of these materials are included.

Other hair treating agents can be included such as silicones, mineral oils, proteins, and protein derivatives, lanolin and lanolin derivatives, fatty acid esters, propylene glycol and the like. These materials are generally present in amounts of less than about 2% by weight.

The products of the present invention should have a pH of less than 6. If necessary, a suitable pH control agent may be added to bring the pH within the range of 3.0 to 6.0.

The formulations of the present invention can be prepared by any conventional method for preparing cationic creme rinse formulations of this type. Suitable methods include mixing the quaternary with the aqueous base and combining whatever thickener, surfactants, dyes and perfumes are necessary. Occasionally, it is necessary to heat the formulations to temperatures in the range of 70° C. This is especially true where waxy materials are used.

It may also be desirable to subject these compositions to high shear using a variety of methods such as homogenization, high speed impellers, orifice plate and the like.

The composition of the present invention will now be illustrated by way of the following examples which are for the purposes of illustration only and not in any way to be taken as limiting. In the following examples all parts and percentages are in weight and all temperatures in degrees Celsius.

EXAMPLE 1

A creme rinse having the following formulation was prepared:

Dimethyl Benzyl Erucyl Ammonium Chloride (75% actives): 0.75%
Cetyl Lactate: 1.00%
Polyquaternium-5 (Reten 1105): 1.00%
Fragrance: 0.25%
Methyl Paraben: 0.08%

Pearlescent Agent: 0.50%
Dilaureth-4 Dimonium Chloride (HOE S 2650): 1.50%
Hydroxyethyl Cellulose (Natrosol 250 HHR): 0.60%
Deionized Water: 93.72%
1% Solution of FD & C Yellow-5: 0.60%

The water and the erucic quaternary, as well as the HOE S 2650 are mixed together and heated up to 71° C. Cetyl lactate is melted and then added to the water and quaternary mixture with a centrifugal mixer for about three minutes. The Natrosol, Reten and methyl paraben are dry blended and then mixed to the above mixture with an impeller for about thirty minutes. The dye is then added and the mixture is cooled to 43° C. The perfume is then added to the batch and the mixture is forced to cool to room temperature.

When tested, this formulation produced a creme rinse composition which gave hair suitable conditioning properties and left a clean, relatively non-coated feel upon the hair.

EXAMPLE 2

The following formulation is prepared by first mixing the water, formaldehyde, and dyes in a kettle and heating to 35° C. The Natrosol is sifted in and mixed for about 20-30 minutes. The quaternary is then added with mixing followed by the ethanol and perfume.

Deionized Water: 91.55%
Formaldehyde (37%) 0.25%
D & C Yellow #10 (1% solution): 1.05%
Natrosol 250 HHR: 0.65%
Dimethyl Benzyl Erucyl Ammonium Chloride (75% actives): 3.00%
Ethanol: 3.00%
Perfume: 0.50%

This formulation produced a clear creme rinse formulation which had good conditioning properties and left a clean feel upon the hair.

EXAMPLE 3

A composition having an anti-dandruff incorporated into the creme rinse was prepared having the following formulation:

Formaldehyde (37%): 0.25%
D & C Yellow #10 (1% Solution): 1.05%
Deionized Water: 90.80%
Natrosol 250 HHR: 0.65%
Dimethyl Benzyl Erucyl Ammonium Chloride (75%): 3.00%
Ethanol: 3.00%
Climbazol: 0.50%
Propylene Glycol: 0.75%

The above formulation was prepared using the procedure of Example 2 except the Climbazol is premixed with the ethanol and the propylene glycol is mixed with the perfume.

This formulation, when tested, provided good creme rinse properties, i.e., no fly-away and good conditioning, while also having a clean feel upon the hair. Furthermore, this product appeared to control dandruff.

EXAMPLE 4

Using the procedure of Example 2, the following formulation was prepared:

Formaldehyde (37%): 0.25%
D & C Yellow #10 (1% Solution): 1.05%
Deionized Water: 89.45%
Natrosol 250 HHR: 0.95%
Dimethyl Benzyl Erucyl Ammonium Chloride (75%): 6.00%
Tween 20 (Polysorbate) (20): 1.00%
Ethanol: 0.80%
Perfume: 0.50%

This formulation produced a clear cream rinse which had good conditioning properties and left a clean feel on the hair.

EXAMPLE 5

Using the procedure of Example 1, the following formulation was prepared:

Dilaureth-4 Dimonium Chloride: 1.50%
FD & C Yellow #5 (0.1%): 0.70%
Dimethyl Benzyl Erucyl Ammonium Chloride (75%): 0.75%
Cetyl Lactate: 1.00%
Polyquaternium-5 (Reten 1101): 1.00%
Natrosol 250 HHR: 0.80%
Preservative: 0.04%
Perfume: 0.25%
Glycerol Monostearate: 1.00%
Stearyl alcohol: 0.75%
Deionized Water: 92.21%

This formulation produced a cream rinse composition which gave good conditioning properties on the hair and provided a clean feel.

EXAMPLE 6

Using the procedure of Example 3, an antidandruff conditioner from the following formulation was prepared:

Deionized Water: 89.19%
Formaldehyde: 0.25%
FD & C Blue-1 (0.1% solution): 0.26%
Natrosol 250 HHR: 0.95%
Ethanol: 2.50%
Dimethyl Benzyl Erucyl Ammonium Chloride (48%): 4.05%
Climbazol: 0.50%
Tween 20 (Polysorbate 20): 1.80%
Perfume: 0.50%

This formulation provided a clear cream rinse formulation having antidandruff activity and also left the hair with good cream rinse properties (i.e. no fly away) while providing a clean feel on the hair.

EXAMPLE 7

Using the procedure of Example 2, the following formulation was prepared:

Formaldehyde (37%): 0.25%
D & C Yellow #10 (1% solution): 1.05%
Deionized Water: 90.05%
Natrosol 250 HHR: 0.65%
Ethanol: 3.00%
Perfume: 0.50%
Dimethyl Benzyl Erucyl Ammonium Chloride (48%): 4.50%

This formulation provided a clear cream rinse formulation having good cream rinse properties and providing a clean feel.

What is claimed is:

1. A hair conditioning composition having good wet combing characteristics, static control and clean feel, said composition comprising:
    (a) An aqueous base
    (b) From about 0.5 to about 10% by weight of quaternary ammonium compound having the formula:

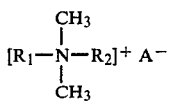

wherein $R_1$ is a mixture of $C_{18}$ to $C_{24}$ alkyls and $C_{18}$ to $C_{24}$ alkenyls, said mixture comprising at least about 65% by weight docosenyl for improved water solubility, clean feel, wet combing characteristics and good static control, less than 15% by weight docosyl and less than about 35% by weight of a mixture of $C_{18}$ to $C_{24}$ alkyls other than docosyl and $C_{18}$ to $C_{24}$ alkenyls other than docosenyl, $R_2$ is selected from methyl, ethyl and benzyl and A is an anion, wherein the composition has a pH within the range of 3 to 6.

2. The composition of claim 1 wherein $R_1$ is a mixture of $C_{18}$ to $C_{24}$ alkyls and $C_{18}$ to $C_{24}$ alkenyls, said mixture comprising at least about 75% by weight docosenyl, less than about 10% by weight docosyl and less than about 15% by weight of a mixture of $C_{18}$ to $C_{24}$ alkyls other than docosyl and $C_{18}$ to $C_{24}$ alkenyls other than docosenyl.

3. The composition of claim 1 wherein the quaternary ammonium composition is dimethyl benzyl erucyl ammonium chloride.

4. The composition of claim 1 wherein the composition includes an effective amount of a water-soluble anti-dandruff agent.

5. The composition of claim 1 wherein said composition includes an effective amount of a thickening agent.

6. A clear hair conditioning composition having good wet combing characteristics, static control and clean feel, said composition comprising:
    (a) An aqueous base, and
    (b) From about 0.5 to 10% by weight of quaternary ammonium compounds having the formula:

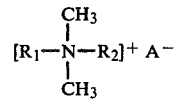

wherein $R_1$ is a mixture of $C_{18}$ to $C_{24}$ alkyls and $C_{18}$ to $C_{24}$ alkenyls, said mixture comprising at least about 80% by weight of docosenyl, for improved water solubility, clean feel, wet combing characteristics and good static control, less than about 9% by weight docosyl and less than 11% of a mixture $C_{18}$ to $C_{24}$ alkenyls other than docosenyl, $R_2$ is selected from methyl, ethyl and benzyl and A is an anion, wherein said composition has a pH within the range of 3 to 6.

7. The composition of claim 6 wherein the quaternary ammonium composition is dimethyl benzyl erucyl ammonium chloride.

8. The composition of claim 6 wherein the composition includes an effective amount of a water-soluble anti-dandruff agent.

* * * * *